(12) United States Patent
Mann

(10) Patent No.: US 8,853,129 B2
(45) Date of Patent: Oct. 7, 2014

(54) SYNERGISTIC HERBICIDAL COMPOSITION CONTAINING PENOXSULAM AND ORYZALIN

(71) Applicant: Richard K. Mann, Franklin, IN (US)

(72) Inventor: Richard K. Mann, Franklin, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/862,726

(22) Filed: Apr. 15, 2013

(65) Prior Publication Data

US 2013/0231245 A1 Sep. 5, 2013

Related U.S. Application Data

(63) Continuation of application No. 13/282,589, filed on Oct. 27, 2011, now abandoned.

(60) Provisional application No. 61/407,486, filed on Oct. 28, 2010.

(51) Int. Cl.
| | |
|---|---|
| *A01N 43/90* | (2006.01) |
| *A01N 43/02* | (2006.01) |
| *A01N 33/18* | (2006.01) |
| *A01N 41/02* | (2006.01) |
| *A01N 41/06* | (2006.01) |

(52) U.S. Cl.
CPC ............... *A01N 43/90* (2013.01); *A01N 41/06* (2013.01)
USPC ............... 504/241; 504/139; 504/355

(58) Field of Classification Search
USPC .................. 504/136, 139, 241, 355
See application file for complete search history.

(56) References Cited

U.S. PATENT DOCUMENTS

2006/0183637 A1* 8/2006 Loughner et al. ............. 504/101

OTHER PUBLICATIONS

Oryzalin, Specimen Label, FarmSaver.com, 2003, online [retrieved Oct. 8, 2012], retrieved from:< http://www2.hawaii.edu/~defrenkpdflecturenotes/HORT_481_Lab_HANDOUTS/herbicide_labels_proj1/Oryzalin_08_25_03.pdf > 4 pages.*
Penoxsulam and Its Use as a Herbicide in Mixtures for Use in Rice, Wheat, . . . and Aquatics, Apr. 2005, The IP.com Journal, vol. 5, No. 4, pp. 286-293.*

* cited by examiner

*Primary Examiner* — Sue Liu
*Assistant Examiner* — Andriae M Holt
(74) *Attorney, Agent, or Firm* — Robert Chang

(57) ABSTRACT

An herbicidal synergistic composition containing (a) penoxsulam and (b) oryzalin provides improved post-emergence herbicidal weed control in tree and vine crops, turf, sugar cane, range and pasture, parks and alleyways, and IVM.

13 Claims, No Drawings

SYNERGISTIC HERBICIDAL COMPOSITION CONTAINING PENOXSULAM AND ORYZALIN

CROSS REFERENCE TO RELATED APPLICATIONS

This application is a continuation of U.S. patent application Ser. No. 13/282,589, filed Oct. 27, 2011 and claims the benefit of U.S. Provisional Patent Application Ser. No. 61/407,486 filed Oct. 28, 2010, the entireties of which are incorporated herein by reference.

FIELD

This invention concerns a synergistic herbicidal composition containing (a) penoxsulam and (b) oryzalin for controlling growth of undesirable vegetation, particularly in fruit trees, including pome fruit, stone fruit, tree nut, citrus, olives, grapevines and other perennial fruit producing trees, as well as in turf, in sugar cane, in parks and alleyways, in range and pasture and in industrial vegetation management (IVM).

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Ninth Edition, 2007, p. 429, "'synergism' [is] an interaction of two or more factors such that the effect when combined is greater than the predicted effect based on the response to each factor applied separately." The present invention is based on the discovery that oryzalin and penoxsulam, already known individually for their herbicidal efficacy, display a synergistic effect when applied in combination.

SUMMARY OF THE INVENTION

The present invention concerns a synergistic herbicidal mixture comprising an herbicidally effective amount of (a) penoxsulam and (b) oryzalin. The compositions may also contain an agriculturally acceptable adjuvant or carrier.

The present invention also concerns a method of controlling the growth of undesirable vegetation, particularly in fruit trees, including pome fruit, stone fruit, tree nut, citrus, olives, grapevines and other perennial fruit producing trees, as well as in turf, in sugar cane, in parks and alleyways, in range and pasture and in industrial vegetation management.

DETAILED DESCRIPTION OF THE INVENTION

Penoxsulam is the common name for (2-(2,2-difluoroethoxy)-N-(5,8-dimethoxy-[1,2,4]triazolo[1,5-c]pyrimidin-2-yl)-6-(trifluoromethyl)benzenesulfonamide. Its herbicidal activity is described in *The Pesticide Manual*, Fifteenth Edition, 2009. Penoxsulam controls barnyard grass, as well as many broadleaf and sedge weeds in rice, turf, tree nut and vineyard crops, cereal and grain crops, and IVM.

Oryzalin is the common name for 4-(dipropylamino)-3,5-dinitrobenzenesulfonamide. Its herbicidal activity is described in *The Pesticide Manual*, Fifteenth Edition, 2009. Oryzalin controls grasses and small seeded broad-leaved weeds in tree nut and vine crops, fruit trees, soybeans and turf.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

Herbicidal activity is exhibited by the compounds of the synergistic mixture when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

In the composition of this invention, the active ingredient ratio (weigh-to-weight, wt:wt) of oryzalin to penoxsulam at which the herbicidal effect is synergistic lies within the range from about 40:1 to about 960:1 with a ratio of about 300:1 being preferred.

The rate at which the synergistic composition is applied will depend upon the particular type of weed to be controlled, the degree of control required, and the timing and method of application. In general, the composition of the invention can be applied at an application rate from about 2005 grams active ingredient per hectare (gai/ha) to about 4850 gai/ha based on the total amount of active ingredients in the composition. An application rate from about 2405 gai/ha to about 4850 gai/ha is preferred. In an especially preferred embodiment of the invention, oryzalin is applied at a rate from about 2400 gai/ha to about 4800 gai/ha, and penoxsulam is applied at a rate from about 6 gai/ha to about 35 gai/ha.

The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: 4-CPA, 4-CPB, 4-CPP, 2,4-D, 3,4-DA, 2,4-DB, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlomitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, oryzalin, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oxadiargyl, oxadiazon, oxapyrazon, oxasulfuron, oxaziclomefone, oxyfluorfen, parafluron, paraquat, pebulate, pelargonic acid, pendimethalin, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac tritosulfuron, vernolate and xylachlor.

The synergistic mixture of the present invention can additionally be employed to control undesirable vegetation in many crops that have been made tolerant to or resistant to them or to other herbicides by genetic manipulation or by mutation and selection. The synergistic mixture of the present invention can be used on acetolactate synthase inhibitor tolerant crops. The synergistic composition of the present invention can, further, be used in conjunction with 2,4-D, glyphosate, glufosinate, dicamba, sulfonylureas or imidazolinones on 2,4-D tolerant, glyphosate-tolerant, glufosinate-tolerant, dicamba-tolerant, sulfonylurea-tolerant crops or imidazolinone-tolerant crops. It is generally preferred to use the synergistic composition of the present invention in combination with herbicides that are selective for the crop being treated and which complement the spectrum of weeds controlled by these compounds at the application rate employed. It is further generally preferred to apply the synergistic composition of the present invention and other complementary herbicides at the same time, either as a combination formulation or as a tank mix.

The synergistic composition of the present invention can generally be employed in combination with known herbicide safeners, such as benoxacor, benthiocarb, brassinolide, cloquintocet (mexyl), cyometrinil, cyprosulfamate, daimuron, dichlormid, dicyclonon, dietholate, dimepiperate, disulfoton, fenchlorazole-ethyl, fenclorim, flurazole, fluxofenim, furilazole, harpin proteins, isoxadifen-ethyl, mefenpyr-diethyl, mephenate, MG 191, MON 4660, naphthalic anhydride (NA), oxabetrinil, R29148 and N-phenyl-sulfonylbenzoic acid amides, to enhance their selectivity.

In practice, it is preferable to use the synergistic composition of the present invention in mixtures containing an herbicidally effective amount of the herbicidal components along with at least one agriculturally acceptable adjuvant or carrier.

Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Oftentimes, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the synergistic composition of the present invention is generally from 0.001 to 98 percent by weight. Concentrations from 0.01 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.05 weight percent.

The present compositions can be applied to weeds or their locus by the use of conventional ground or aerial dusters, sprayers, and granule applicators, by addition to irrigation water, and by other conventional means known to those skilled in the art.

The following examples illustrate the present invention.

Examples

Evaluation of Postemergence Herbicidal Activity of Mixtures Under Field Conditions Methodology Trials were conducted under field conditions in France. Trial sites were located in commercially grown European grape crop (*Vitis vinifera*). The grapes were grown using normal cultural practices for fertilization, seeding, and maintenance to ensure good growth of the crop and the weeds. The trials were conducted using normal research methodology.

Trial plots were between 2 to 4.5 meters (m) wide by 5.5 to 10 m long. All treatments were applied using a randomized complete block trial design with 3 or 4 replications per treatment. The trial sites had naturally occurring populations of weeds. The weed spectrum included, but was not limited to, black nightshade (*Solanum nigrum*; SOLNI), common lambsquarter (*Chenopodium album*; CHEAL), common groundsel (*Senecio vulgaris*; SENVU), round-leaved fluellen (*Kickxia spuria*; KICSP) and common purslane (*Portulaca olerace*; POROL).

Treatments consisted of tank mixes of an oil dispersion of penoxsulam and commercially available formulations of oryzalin. Glyphosate was tank mixed with all treatments to provide complete foliar control of all weeds so that the residual weed control after application could be evaluated. The application volumes were between 150-325 liters per hectare (L/ha) of water. All application were made using precision gas hand sprayers using a 2 or 3 m boom using flat fan (80° or 110°) nozzles to broadcast the treatments on the soil.

Evaluation

The treated plots and control plots were rated blind at various intervals after application. Ratings were based of Percent (%) Visual weed control, where 0 corresponds to no injury and 100 corresponds to complete kill.

Data were collected for all trials and analyzed using various statistical methods.

Colby's equation was used to determine the herbicidal effects expected from the mixtures (Colby, S. R. Calculation of the synergistic and antagonistic response of herbicide combinations. *Weeds* 1967, 15, 20-22).

The following equation was used to calculate the expected activity of mixtures containing two active ingredients, A and B:

Expected=$A+B-(A \times B/100)$

A=observed efficacy of active ingredient A at the same concentration as used in the mixture;
B=observed efficacy of active ingredient B at the same concentration as used in the mixture.

The results are summarized in Tables 1 through 2.

TABLE 1

Synergistic weed control following an application of Penoxsulam + Oryzalin 56 to 109 days after application

| Application Rate (g ai/ha) | | Percent Control | | | | | |
|---|---|---|---|---|---|---|---|
| | | SOLNI (1) | | SOLNI (2) | | CHEAL | |
| Penoxsulam | Oryzalin | Ob | Ex | Ob | Ex | Ob | Ex |
| 5.6 | 0 | 78 | — | — | — | — | — |
| 0 | 3,000 | 0 | — | — | — | — | — |
| 5.6 | 3,000 | 99 | 78 | — | — | — | — |
| 7 | 0 | — | — | 17 | — | 13 | — |
| 0 | 2,400 | — | — | 25 | — | 13 | — |
| 7 | 2,400 | — | — | 94 | 38 | 43 | 24 |

SOLNI (1) - 56 DAA, Bourdic, France
SOLNI (2) - 68 DAA, Eshallat, France
CHEAL - 109 DAA, Fronton, France
SOLNI - black nightshade (*Solanum nigrum*)
CHEAL - common lambsquarter (*Chenopodium album*)
g ai/ha - grams of active ingredient per hectare
Obs - percent control observed
Ex - percent control expected by Colby equation

TABLE 2

Synergistic weed control following an application of Penoxsulam + Oryzalin 103 days after application in Fronton, France.

| Application Rate (g ai/ha) | | Percent Control | | | | | |
|---|---|---|---|---|---|---|---|
| | | POROL | | KICSP | | SENVU | |
| Penoxsulam | Oryzalin | Ob | Ex | Ob | Ex | Ob | Ex |
| 7 | 0 | 0 | | 0 | | 27 | |
| 0 | 2,400 | 80 | | 0 | | 23 | |
| 7 | 2,400 | 100 | 80 | 43 | 0 | 60 | 44 |

POROL - common purslane (*Portulaca oleracea*)
KICSP - round-leaved fluellen (*Kickxia spuria*)
SENVU - common groundsel (*Senecio vulgaris*)
g ai/ha - grams of active ingredient per hectare
Obs - percent control observed
Ex - percent control expected by Colby equation

What is claimed is:

1. A synergistic herbicidal composition comprising a herbicidally effective amount of (a) oryzalin and (b) penoxsulam, wherein the weight ratio of oryzalin:penoxsulam is from about 343:1 to about 536:1.

2. The composition of claim 1, wherein the weight ratio of oryzalin:penoxsulam is about 343:1 or 536:1.

3. The composition of claim 1 further comprising an agriculturally acceptable adjuvant or carrier.

4. A method of controlling undesirable vegetation comprising contacting the vegetation or the locus thereof with a herbicidally effective amount the composition of claim 1.

5. A method of controlling undesirable vegetation comprising contacting the vegetation or the locus thereof with a herbicidally effective amount of (a) oryzalin and (b) penoxsulam, wherein the weight ratio of oryzalin:penoxsulam is from 343:1 to 536:1.

6. The method of claim 5, wherein the weight ratio of oryzalin:penoxsulam is about 343:1 or 536:1.

7. The method of claim 5, wherein the undesirable vegetation is *Solanum nigrum, Chenopodium album, Portulaca oleracea, Kickxia spuria*, or *Senecio vulgaris*.

8. The method of claim 5, wherein the undesirable vegetation is controlled in fruit trees, grapevines, turf, sugar cane, parks and alleyways, range and pasture, or industrial vegetation management.

9. The method of claim 8, wherein the fruit tree is pome, stone, tree nut, citrus or olive.

10. The method of claim 5, wherein the oryzalin is applied at a rate of from about 2400 gai/ha to about 4800 gai/ha and the penoxsulam is applied at a rate of from about 5.6 gai/ha to about 35 gai/ha.

11. The method of claim 9, wherein the oryzalin is applied at a rate of about 2400 gai/ha to about 3000 gai/ha and the penoxsulam is applied at a rate of from about 5.6 gai/ha to about 7 gai/ha.

12. The method of claim 9, wherein the penoxsulam is applied at a rate of about 5.6 gai/ha and the oryzalin is applied at a rate of about 3000 gai/ha.

13. The method of claim 5, wherein the penoxsulam is applied at a rate of about 7 gai/ha and the oryzalin is applied at a rate of about 2400 gai/ha.

* * * * *